(12) United States Patent
Hruby et al.

(10) Patent No.: US 8,518,951 B2
(45) Date of Patent: Aug. 27, 2013

(54) ANTI-ARENAVIRAL COMPOUNDS

(75) Inventors: Dennis E. Hruby, Albany, OR (US);
Tove C. Bolken, Keizer, OR (US);
Dongcheng Dai, Corvallis, OR (US)

(73) Assignee: Siga Technologies, Inc., Corvallis, OR (US)

( * ) Notice: Subject to any disclaimer, the term of this patent is extended or adjusted under 35 U.S.C. 154(b) by 0 days.

(21) Appl. No.: 13/338,726

(22) Filed: Dec. 28, 2011

(65) Prior Publication Data

US 2012/0107276 A1   May 3, 2012

Related U.S. Application Data

(62) Division of application No. 12/162,395, filed as application No. PCT/US2007/002570 on Jan. 31, 2007, now Pat. No. 8,106,058.

(60) Provisional application No. 60/763,921, filed on Feb. 1, 2006.

(51) Int. Cl.
*A61K 31/4965* (2006.01)

(52) U.S. Cl.
USPC .................................................. 514/255.01

(58) Field of Classification Search
USPC .................................................. 514/255.01
See application file for complete search history.

(56) References Cited

U.S. PATENT DOCUMENTS

| 7,687,641 B2 | 3/2010 | Jordan et al. |
| 2002/0111378 A1 | 8/2002 | Stamos et al. |
| 2007/0254934 A1 | 11/2007 | Hruby |
| 2007/0287735 A1 | 12/2007 | Jordan et al. |
| 2008/0300265 A1 | 12/2008 | Hruby |
| 2009/0036513 A1 | 2/2009 | Hruby |
| 2009/0180980 A1 | 7/2009 | Hruby |
| 2009/0203675 A1 | 8/2009 | Deng et al. |

FOREIGN PATENT DOCUMENTS

| JP | 2009-519265 A | 5/2009 |
| WO | WO2004099179 A1 | 11/2004 |
| WO | WO 2005037257 | 4/2005 |
| WO | WO 2006/062898 | 6/2006 |
| WO | WO2006062898 A2 | 6/2006 |
| WO | WO2007068380 A1 | 6/2007 |
| WO | WO 2007/103111 | 9/2007 |
| WO | WO 2007/120374 | 10/2007 |
| WO | WO2008079159 A2 | 7/2008 |
| WO | WO 2007/100888 | 9/2008 |
| WO | WO2008130348 A1 | 10/2008 |
| WO | WO 2008147474 | 12/2008 |
| WO | WO2008147474 A2 | 12/2008 |
| WO | WO2008147962 A1 | 12/2008 |
| WO | WO2009029622 A2 | 3/2009 |
| WO | WO2009123776 A2 | 10/2009 |
| WO | WO2009149054 A1 | 12/2009 |

OTHER PUBLICATIONS

Nandan Prasad R. et al., "Potential Antihypertensive Agents. IV. Unsymmetrically 1, 4-Disubstituted Piperazines. II"J. Medicinal Chem., vol. 12, No. 3, May 1969, pp. 551-552.
Pandey B.R. et al., "4 Arylaminothiocarbonyl-1-1-0-Methoxyphenylc Arbamidoethyl Piperazines as Anti Convulsants", Journal of Heterocyclic Chemistry, vol. 17, No. 5, 1980, pp. 1119-1120.
European Search Report, Application No. 07 76 9434, Dated Jun. 9, 2011.
Broken et al. Identification and Characterization of potent small molecule Inhibitor of hemorrhagic fever new world arenaviruses. Antiviral Reasearch, Mar. 2005, vol. 65.
Golf et al. A survey of antiviral drugs for bioweapons, Antiviral Chemistry and Chemotherapy, 2005, vol. 16, pp. 283-294.
Co-pending U.S. Appl. No. 12/673,963 ; Inventor Dal et al. ; filed Feb. 18, 2010.
Chemical compound: 4-methyl-piperazine-1-carbothioic acid (3,4-dichloro-phenyl)-amide. Source: Chemical Diversity, renamed ChemDiv, San Diego, CA 92121. Catalog number is no longer available, 2005.
Chemical compound: 4-ethyl-piperazine-1-carbothioic acid (3, 4-dichloro-phenyl)-amide. Source: Chemical Diversity, renamed ChemDiv, San Diego, CA, 92121. Catalog No. is K781-0449, 2005.
Chemical compound: 4-methyl-piperazine-1-carboxylic acid (3,4-dichloro-phenyl)-amide. Source: Chemical Diversity, renamed ChemDiv, San Diego, CA, 92121. Catalog number is no longer available, 2005.

*Primary Examiner* — Shengjun Wang
(74) *Attorney, Agent, or Firm* — Kramer Levin Naftalis & Frankel LLP

(57) ABSTRACT

Described herein are 4-methyl-piperazine-1-carbothioic acid amide derivatives and analogs, as well as compositions containing the same, for the treatment or prophylaxis of viral infections and diseases associated therewith, particularly those viral infections and associated diseases caused by hemorrhagic fever viruses, such as Arenaviruses.

8 Claims, No Drawings

ANTI-ARENAVIRAL COMPOUNDS

This application is a divisional of U.S. application Ser. No. 12/162,395 filed Nov. 4, 2008 which is a national stage filing of corresponding international application number PCT/US2007/02570, filed on Jan. 31, 2007, which claims priority of U.S. Provisional Application No. 60/763,921, filed Feb. 1, 2006, all of which are hereby incorporated by reference in their entirety.

STATEMENT REGARDING FEDERALLY SPONSORED RESEARCH OR DEVELOPMENT

This invention was made with U.S. government support under Grant No. 17R43 AI056525-01 awarded by the National Institute of Health (NIH). The U.S. Government has certain rights in the invention.

FIELD

Described herein are 4-methyl-piperazine-1-carbothioic acid amide derivatives and analogs, as well as compositions containing the same, for the treatment or prophylaxis of viral infections and diseases associated therewith, particularly those viral infections and associated diseases caused by hemorrhagic fever viruses, such as Arenaviruses.

BACKGROUND

The family Arenaviridae consists of a single genus (Arenavirus) that includes several viruses. Rodents are the primary reservoirs of Arenaviruses, and human infection is thought to occur by contact with infectious rodent excreta. Two groups of Arenaviruses are currently recognized. The Old World group (lymphocytic choriomeningitis (LCM)-Lassa complex) includes viruses indigenous to Africa and the ubiquitous LCM virus. The New World group (Tacaribe complex) includes viruses indigenous to the Americas. Several Arenaviruses are associated with severe hemorrhagic disease in humans. Lassa virus (from the Old World group) is responsible for Lassa hemorrhagic fever, while four viruses from the New World group (all from Clade B) cause severe hemorrhagic fever in humans. Those viruses are Junin virus, which is responsible for Argentine hemorrhagic fever; Machupo virus, which is responsible for Bolivian hemorrhagic fever; Guanarito virus, which is responsible for Venezuelan hemorrhagic fever; and Sabiá virus, which was isolated from a fatal case of hemorrhagic fever in Brazil. It is estimated that Lassa virus causes 100,000-300,000 infections and approximately 5,000 deaths annually. So far an estimated 30,000 confirmed cases of Junin infections have been documented, while about 2,000 of Machupo, 200 of Guanarito and only 2 of Sabiá.

Recent concerns over the use of Arenaviruses as biological weapons have underscored the necessity of developing small-molecule therapeutics that target these viruses. These Arenaviruses are a serious biowarfare threat because of: (i) their high disease morbidity and mortality (case fatality rates of 15-30%); (ii) their ease of dissemination and aerosol transmissibility; and (iii) the ease of obtaining and producing large quantities of these viruses.

Currently, there are no specific treatments approved for use against Arenavirus hemorrhagic fevers. Present disease management consists of general supportive care—monitoring and correcting fluid, electrolyte and osmotic imbalances and treating hemorrhage with clotting factor or platelet replacement. Convalescent immune serum therapy may be effective in treating cases of Junin and Machupo virus disease, but the availability of such serum is extremely limited.

Ribavirin, a nucleoside analog, has been used with some success in Lassa fever patients. In small trials, intravenous ribavirin given to patients within the first 6 days after development of fever decreased mortality from 76% to 9%. A controlled trial of 18 patients with Argentine hemorrhagic fever resulted in 13% mortality in treated patients, compared with 40% mortality in untreated patients. However, Ribavirin therapy is associated with adverse effects, including a dose-related, reversible hemolytic anemia, and also has demonstrated teratogenicity and embryo lethality in several animal species. It is therefore classified as a pregnancy category X drug, contraindicated during pregnancy. Intravenous ribavirin is available in limited supplies in the U.S. for compassionate use under en IND application. The dosing regimen for ribavirin therapy that has been used in cases of Lassa fever consists of an initial 30 mg/kg intravenous (IV) loading dose, followed by 16 mg/kg IV every 6 hours for 4 days; then 8 mg/kg IV every 8 hours for 6 days (total treatment time 10 days). The cost of treatment for an adult male is approximately $800. The attributes of ribavirin make it less than ideal for the treatment of Arenavirus hemorrhagic fevers.

A number of in vitro inhibitors of Arenavirus replication have been reported in the literature including phenothiazines, trifluoroperazine and chlorpromazine amantadine brassinosteroids, and actinomycin D. The anti-Arenavirus activities of these compounds are generally weak and non-specific.

The only Arenavirus hemorrhagic fever for which studies have been undertaken toward development of a vaccine has been Argentine hemorrhagic fever (AHF) caused by Junin virus. A live-attenuated vaccine, called Candid 1, has been evaluated in controlled trials among agricultural workers in AHF-endemic areas, where it appeared to reduce the number of reported AHF cases with no serious side effects. It is not known if the Candid 1 vaccine would be useful against other Arenavirus hemorrhagic fevers and this vaccine is not available in the United States of America.

Based on these data, new therapies and preventives are clearly needed for infections and diseases caused by Arenavirus infection.

All human pathogenic Arenaviruses from the New World group causing hemorrhagic fever are from the Clade B. These human pathogen viruses require manipulation under high-level containment (BSL-4). However, Amapari and Tacaribe viruses, which are also from Clade B, can be grown in tissue culture under BSL-2 (low-level) containment. Working under low-level containment makes experimentation easier and safer with these viruses. While Amapari virus produces low cytopathic effect, Tacaribe virus can be grown readily in cell culture and produce robust CPE in 4 to 6 days. Since this CPE is directly related to viral replication, compounds that inhibit virus replication in cell culture can be identified readily as conferring protection from virus-induced CPE (although it is theoretically possible to inhibit CPE without inhibiting virus replication). Moreover, compounds having identified activity against Tacaribe virus will also likely be active against Arenavirus human pathogen causing hemorrhagic fever (Junin, Machupo, Guanarito and Sabiá given the high degree of homology (around 70% identity for all 4 proteins of Tacaribe virus compared to Junin virus, with long stretch of protein with perfect identity) between these viruses.

SUMMARY

Described herein are compounds, compositions, and methods for the treatment and prophylaxis of viral infections, as well as diseases associated with viral infections in living hosts. The compounds described herein are of the following general formula:

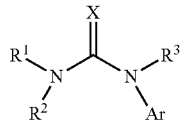

wherein $R^1$, $R^2$ and $R^3$ are independently hydrogen alkyl, alkenyl, alkynyl, or unsubstituted or substituted cycloalkyl, arylalkyl, aryl, or $R^1$ and $R^2$ together may form a substituted or unsubstituted ring, which may include one or more heteroatoms in the ring;

X is O or S; and

Ar is substituted or unsubstituted aryl or heteroaryl;

said cycloalkyl, arylalkyl, and aryl group substituents being one or more radicals(s) independently selected from the group consisting of a straight- or branched chain alkyl, alkoxy, alkoxyalkyl, alkoxyalkoxy, halogen, polyfluoroalkyl, polyfluoroalkoxy, carboxy, cyano, nitro, amido, amidoalkyl, carboxamide, alkylthio, alkylsulfinyl, alkylsulfonyl, sulfonamide, and mercapto;

or a pharmaceutically acceptable salt thereof.

Also described herein are pharmaceutical compositions containing the antiviral compounds of Formula 1 and corresponding methods of use for treating and preventing Infections caused by arenaviruses.

DETAILED DESCRIPTION

Provided herein are compounds of the following general formula

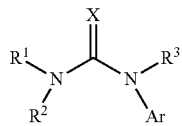

wherein $R^1$, $R^2$ and $R^3$ are independently hydrogen, alkyl, alkenyl, alkynyl, or unsubstituted or substituted cycloalkyl, arylalkyl, aryl, or $R^1$ and $R^2$ together may form a substituted or unsubstituted ring, which may include one or more heteroatoms in the ring;

X is O or S; and

Ar is substituted or unsubstituted aryl or heteroaryl;

said cycloalkyl, arylalkyl, and aryl group substituents being one or more radical(s) independently selected from the group consisting of a straight- or branched chain alkyl, alkoxy, alkoxyalkyl, alkoxyalkoxy, halogen, polyfluoroalkyl, polyfluoroalkoxy, carboxy, cyano, nitro, amido, amidoalkyl, carboxamide, alkylthio, alkylsulfinyl, alkylsulfonyl, sulfonamide, and mercapto;

or a pharmaceutically acceptable salt thereof.

Exemplary compounds of Formula 1 include compounds wherein $R^1$ and $R^2$ together form a substituted or unsubstituted ring. That ring may comprise a heteroatom, such as nitrogen. Such ring moieties include piperidine, piperazine, pyrazolidine, and pyrrolidine. The ring may be mono-substituted; the substituent may be an alkyl group, such as an ethyl or methyl group. Such a substituent may appear at, for example, the 4-position on the ring.

Exemplary compounds of Formula 1 will also include compounds wherein $R^3$ is hydrogen.

Exemplary compounds of Formula 1 will also include compounds wherein Ar is a substituted aryl group, such as a phenyl group. The phenyl group may have one or more substituents (e.g., di-substituted phenyl). The substituents may be, for example, halogen atoms, such as chlorine or fluorine.

Specific compounds which are disclosed herein to be useful in the prevention and treatment of arenavirus infection include the compounds shown in the following table:

| Formula | Name | Structure |
|---|---|---|
| $C_{12}H_{15}Cl_2N_3S$ | 4-methyl-piperazine-1-carbothioic acid (3,4-dichloro-phenyl)-amide | 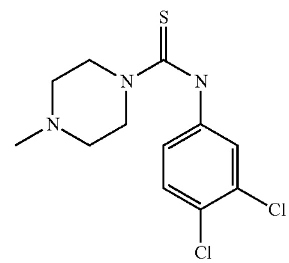 [SMILES: CN1CCN(C(=S)Nc2ccc(Cl)c(Cl)c2)CC1] |
| $C_{13}H_{17}Cl_2N_3S$ | 4-ethyl-piperazine-1-carbothioic acid (3,4-dichloro-phenyl)-amide | 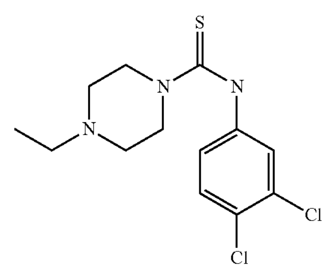 [SMILES: CCN1CCN(C(=S)Nc2ccc(Cl)c(Cl)c2)CC1] |
| $C_{12}H_{15}Cl_2N_3O$ | 4-methyl-piperazine-1-carboxylic acid (3,4-dichloro-phenyl)-amide | 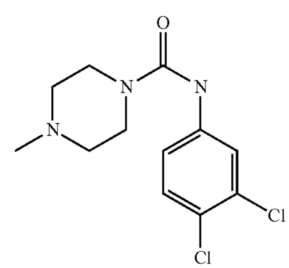 [SMILES: CN1CCN(C(=O)Nc2ccc(Cl)c(Cl)c2)CC1] |

Also described herein is a method for preventing and treating arenavirus infections and for preventing and treating diseases associated with such infections in a living host (for example, a mammal including a human) having or susceptible to an arenavirus infection, comprising the step of administering to the living host a therapeutically effective amount of a compound of the formula:

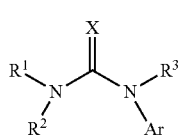

wherein $R^1$, $R^2$, $R^3$, X, and Ar are as defined for compounds of Formula 1 above, or a pharmaceutically acceptable salt to a host susceptible to, or suffering from such infection.

A particular method includes the prevention and treatment of arenavirus infections and diseases associated with such infections in a living host having or susceptible to an arenavirus infection, comprising the step of administering a therapeutically effective amount of the compounds of the Formula 1, above, or a pharmaceutically acceptable salt thereof.

Also described herein are methods for the treatment or prevention of infections caused by an arenavirus wherein the arenavirus is selected from the group consisting of Lassa virus, Junin virus, Machupo virus, Guanarito virus, and Sabiá virus in a living host (for example, a mammal including a human) comprising the step of administering a therapeutically effective amount of the compounds described herein to a host susceptible to, or suffering from such infection.

Also described herein are pharmaceutical compositions for the treatment or prevention of arenavirus infections and diseases associated with such infections in a living host, that comprise a therapeutically effective amount of one or more of the compounds of the formula:

$$\underset{R^2}{\overset{R^1}{N}}\underset{Ar}{\overset{X}{\underset{\|}{C}}}\underset{Ar}{\overset{R^3}{N}} \quad 1$$

wherein $R^1$, $R^2$, $R^3$, X, and Ar are as defined for compounds of Formula 1 above, and a pharmaceutically acceptable carrier therefor.

The compounds described herein, their isomers and pharmaceutically acceptable salts exhibit antiviral activity. The compounds described herein are particularly effective against arenaviruses, and are useful in the prophylaxis and/or treatment of infections and diseases associated with this virus in living hosts. Examples of arenaviruses that may be treated or prevented using the compounds and compositions described herein include, but are not limited to Lassa virus, Junin virus, Machupo virus, Guanarito virus, and Sabiá virus.

In vitro cell-based studies have been performed that demonstrate the usefulness of compounds described herein as antiviral agents. For example, antiviral activity of representative compounds was evaluated in assays that measure the ability of compounds to protect cells from virus-induced CPE. Cells that will support growth of the particular arena virus strain are seeded into 96-well tissue culture treated plates and then infected with an amount of the appropriate arena virus strain that results in complete CPE in about 7 days. Various dilutions of inhibitory compound(s) are added and the plates are incubated at the appropriate temperature for optimal virus growth. At the end of the incubation period, cells are fixed with glutaraldehyde and stained with crystal violet. Cell protection is measured spectrophotometrically at $OD_{570}$ nm. The interpolated compound dilution that results in 50% protection of the cell monolayer from virus-induced CPE is calculated and reported as the 50% effective concentration or $EC_{50}$. Antiviral activity of representative compounds described herein occurred at drug concentrations that had no demonstrable effect on cell growth, indicating that the compounds were working specifically by an antiviral mechanism.

The compounds described herein are, collectively, the compounds of Formula 1, pharmaceutically acceptable salts thereof, their isomers, and mixtures thereof. Compounds are identified herein by their chemical structures and/or chemical names. Where a compound is referred to by both a chemical structure and a chemical name, and that chemical structure and chemical name conflict, the chemical structure is determinative of the compound's identity.

The term "living host" as used herein refers to an organism that is living and capable of being infected with a virus, such as an arenavirus; for example, a mammal, which includes a human.

The term "alkyl" as used herein refers to straight or branched chain aliphatic hydrocarbon radicals of 4 to 4 carbon atoms, optionally up to 6 carbon atoms or as high as 10 or more carbon atoms. Similarly, the term "alkyl", or any variation thereof, used in combination form to name substituents, such as alkoxy alkylthio (—S-alkyl), monoalkylamino (—NH-alkyl), dialkylamino, (—N-(alkyl)alkyl), alkylsulfonyl (—S(O)$_2$-alkyl), carboxyalkyl (—alkyl-COOH), or the like, also refers to aliphatic hydrocarbon radicals of one to four carbon atoms, optionally one to six carbon atoms. Also "alk" in structural formula denotes an alkyl group, unless divalency is indicated in which case the "alk" denotes the corresponding alkylene group(s). Additionally, the term "lower alkyl" denotes an alkyl group having one to four carbon atoms.

The term "alkenyl" as used herein refers to straight or branched chain aliphatic hydrocarbon radicals of 2 to 7 carbon atoms containing one double bond. Such alkenyl moieties may exist in the E or Z configurations; the compounds described herein include both configurations. The term "alkynyl" as used herein refers to straight or branched chain aliphatic hydrocarbon radicals containing 2 to 7 carbon atoms having at least one triple bond.

The term "phenyl" as used herein refers to a group. A "substituted phenyl" refers to a phenyl group that is substituted with the indicated substituents.

As used herein, the term "aryl", when used as such, refers to an aromatic carbocyclic group, having 6 to 10 carbon atoms including without limitation phenyl and napthyl.

The term "heteroaryl," as used herein, refers to a 5- or 6-membered aromatic cyclic group having at least one carbon atom and one or more oxygen, nitrogen or sulfur atoms in the ring, as for example furyl, thienyl, pyridyl, pyrrolyl, oxazolyl, thiazolyl, imidazolyl, pyrazolyl, isoxazolyl, isothiazolyl, 1,2,3-oxadiazolyl, 1,2,3-triazolyl, tetrazolyl, and the like, including all position isomers. Suitable heteroaryl groups include, but are not limited to, pyridine, thiazole and thiophene.

As used herein, the term "cycloalkyl" refers to a saturated hydrocarbon ring. Cycloalkyls can be monocyclic or can be fused, spiro or bridged bicyclic or tricyclic ring systems. Monocyclic cycloalkyl rings contain from 3 to 7 carbon atoms, optionally from 3 to 18 carbon atoms, as for example cyclopropyl, cyclobutyl, cyclopentyl, and cyclohexyl. Bicyclic and tricyclic cycloalkyl rings contain from 7 to 19 carbon atoms, optionally from 7 to 28 carbon atoms, in the ring system; and include, for example, adamantyl, bicyclo[2.2.1]heptyl, bicyclo[2.2.2]cyclooctanyl, tricyclo[3.2.2.02,4]nonyl, and norbornyl, and bicyclo[3.2.2]nonyl. As used herein, the term "cycloalkenyl" refers to an unsaturated hydrocarbon ring. Cycloalkenyl rings are non-aromatic and contain one or more carbon-carbon double bonds. Cycloalkenyl rings are monocyclic, or are fused, spiro or bridged bicyclic or tricyclic ring systems. Monocyclic cycloalkenyl rings contain from 5 to 7 carbon atoms, optionally from 5 to 10 carbon atoms, and include, for example, cyclopropenyl, cyclobutenyl, cyclopentenyl, and cyclohexenyl. Bicyclic and tricyclic cycloalkenyl rings contain from 7 to 19 carbon atoms in the ring, optionally from 7 to 28 carbon atoms, in the ring system; and include, for example, bicyclo[2.2.1]hept-2-ene, bicyclo[2.2.2]cyclooct-2-enyl; tricyclo[3.2.2.02,4]non-5-enyl, and bicyclo[3.2.2]non-6-enyl.

The term "amido," as used herein, refers to a radical or substituent of the formula —NR"C(=O)R'", wherein R" and R'" represent hydrogen or alkyl.

The term "carboxamide," as used herein, refers to a radical or substituent of the formula —C(=O)—NR"R'", wherein R" and R'" are as previously defined.

The term "sulfonamide," as used herein, refers to a radical or substituent of the formula —SO$_2$NR"R'" or —NR"SO$_2$R'", wherein R" and R'" are as previously defined.

The term "halogen," as used herein, refers to a radical or substituent selected from the group consisting of chloro, bromo, iodo, and fluoro.

The term "HPLC," as used herein, refers to high-performance liquid chromatography.

"Substituted" is intended to indicate that one or more hydrogens on the atom indicated in the expression using "substituted" is replaced with a selection from the indicated group(s), provided that the indicated atom's normal valency is not exceeded, and that the substitution results in a stable compound. When a substituent is an oxo (=O) group, then 2 hydrogens on the atom are replaced.

The compounds described herein and their pharmaceutically acceptable salts are useful in treating and preventing viral infections and diseases in living hosts when used in combination with other active agents, including but not limited to interferons, ribavirin, immunoglobulins, immunomodulators, anti-inflammatory agents, antibiotics, antivirals, anti-infectious agents, and the like.

Compounds described herein are also useful in preventing or resolving arena viral infections in cell, tissue or organ cultures and other in vitro applications. For example, inclusion of compounds described herein as a supplement in cell or tissue culture growth media and cell or tissue culture components will prevent viral infections or contaminations of cultures not previously infected with viruses. Compounds described above may also be used to eliminate or attenuate viral replication in cultures or other biological materials infected or contaminated with viruses (for example, blood), after a suitable treatment period, under any number of treatment conditions as determined by the skilled artisan.

The compounds described herein can form useful salts with inorganic and organic acids such as hydrochloric, sulfuric, acetic, lactic, or the like and with inorganic or organic bases such as sodium or potassium hydroxide, piperidine, ammonium hydroxide, or the like. The pharmaceutically acceptable salts of the compounds of Formula 1 are prepared following procedures that are familiar to those skilled in the art.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication commensurate with a reasonable benefit/risk ratio.

To the extent that certain compounds described herein may have at least one chiral center, the compounds may thus exist as enantiomers. In addition, the compounds described herein may also possess two or more chiral centers and thus may also exist as diastereomers or as exo or endo isomers. Where the processes for the preparation of the present compounds give rise to a mixture of stereoisomers, these isomers may be separated by conventional techniques such as preparative chromatography. Accordingly, the compounds may be prepared as a racemic mixture or, by either enantiospecific synthesis or resolution, as individual enantiomers. The compounds may, for example, be resolved from a racemic mixture into their component racemates by standard techniques, such as the formation of diastereomeric pairs by salt formation with an optically active acid, such as (−)-di-p-toluoyl-d-tartaric acid and/or (+)-di-p-toluoyl-1-tartaric acid followed by fractional crystallization and regeneration of the free base. The racemic mixture may also be resolved by formation of diastereomeric esters or amides, followed by chromatographic separation and removal of the chiral auxiliary. Alternatively, the compounds may be resolved using a chiral HPLC column. It is to be understood that all such isomers and mixtures thereof are encompassed within the scope of subject matter described herein.

The compounds described herein are useful for treating arenavirus infection in living hosts, for example, mammals including humans. When administered to a living host the compounds can be used alone, or as a pharmaceutical composition.

Pharmaceutical compositions comprising the compounds described herein, either alone or in combination with each other, offer a treatment against arenavirus infection. The antiviral pharmaceutical compositions described herein comprise one or more of the compound(s) of Formula 1 above, as the active ingredient in combination with a pharmaceutically acceptable carrier medium or auxiliary agent.

The composition may be prepared in various forms for administration, including tablets, caplets, pills or dragees, or can be filled in suitable containers, such as capsules, or, in the case of suspensions, filled into bottles. As used herein, "pharmaceutically acceptable carrier medium" includes any and all solvents, diluents, or other liquid vehicle, dispersion or suspension aids, surface active agents, isotonic agents, thickening or emulsifying agents, preservatives, solid binders, lubricants and the like, as suited to the particular dosage form desired. Remington's Pharmaceutical Sciences, Twentieth Edition, A. R. Gennaro (William and Wilkins, Baltimore, Md., 2000) discloses various carriers used in formulating pharmaceutical compositions and known techniques for the preparation thereof. Except insofar as any conventional carrier medium is incompatible with the antiviral compounds described herein, such as by producing any undesirable biological effect or otherwise interacting in a deleterious manner with any other component(s) of the pharmaceutical composition, its use is contemplated to be within the scope of the compositions described herein.

In the pharmaceutical compositions described herein, the active agent may be present in an amount of at least 0.5% and generally not more than 90% by weight, based on the total weight of the composition, including carrier medium and/or auxiliary agent(s), if any. Alternatively, the proportion of active agent varies between 5 to 50% by weight of the composition.

Pharmaceutical organic or inorganic solid or liquid carrier media suitable for enteral or parenteral administration can be used to make up the composition. Gelatine, lactose, starch, magnesium stearate, talc, vegetable and animal fats and oils, gum, polyalkylene glycol, or other known medicament components may all be suitable as carrier media or excipients.

The compounds described herein may be administered using any amount and any route of administration effective for attenuating infectivity of the virus. Thus, the expression "amount effective to attenuate infectivity of virus," as used herein, refers to a nontoxic but sufficient amount of the antiviral agent to provide the desired prophylaxis and/or treatment of viral infection. The exact amount required will vary from subject to subject, depending on the species, age, and general condition of the subject, the severity of the infection, the particular antiviral agent, its mode of administration, and the like.

The antiviral compounds described herein may be usefully administered within 24 hours of symptom onset, but therapeutic benefit may be conferred by first administering the compounds within 24-48 hours of symptom onset, or within 48-72 hours of symptom onset. Symptoms of initial arenavirus infections depend on the exact virus contracted. For example, the initial symptoms of infection may include fever, malaise, head and body aches, and sometimes vomiting.

The antiviral compounds described herein may be formulated in dosage unit form for ease of administration and uniformity of dosage. "Dosage unit form," as used herein, refers to a physically discrete unit of antiviral agent appropriate for the patient to be treated. Each dosage should contain the quantity of active material calculated to produce the desired therapeutic effect either as such, or in association with the selected pharmaceutical carrier medium and/or the supplemental active agent(s), if any. Typically, the antiviral compounds described herein will be administered in dosage units containing from about 10 mg to about 10,000 mg of the antiviral agent by weight of the composition, with a range of about 100 mg to about 2,000 mg being typical.

The antiviral compounds described herein may be administered orally, rectally, parenterally, such as by intramuscular injection, subcutaneous injection, intravenous infusion or the like, intracisternally, intravaginally, intraperitoneally, locally, such as by powders, ointments, or drops, or the like, or by inhalation, such as by aerosol or the like, taking into account the nature and severity of the infection being treated. Depending on the route of administration, the antiviral compounds described herein may be administered at dosage levels of about 0.125 to about 250 mg/kg of subject body weight per dose, one or more times a day, to obtain the desired therapeutic effect.

The antiviral compounds described herein will typically be administered from 1 to 4 times a day so as to deliver the above-mentioned daily dosage. However, the exact regimen for administration of the compounds and compositions described herein will necessarily be dependent on the needs of the individual host or patient being treated, the type of treatment administered and the judgment of the attending medical specialist.

For prophylaxis, antiviral compounds described herein are effectively administered within 48 hours post-exposure, although useful prophylactic effects may be obtained by administration seven or even 14 days after possible exposure. The dosages may be essentially the same, whether for treatment or prophylaxis of virus infection.

The antiviral compounds described herein may be effectively administered in combination with other antiviral agents or other antiviral therapies, as part of combination therapy. Such antiviral agents are known in the art, and include zidovudine (azidothymidine; AZT), acyclovir, ganciclovir, vidarabidine, idoxuridine, trifluridine, foscarnet, interferon, amantadine, rimantadine, ribavirin, and related compounds. Other antiviral therapies include, but are not limited to, interferon (IFN) administration and anti-sense RNA treatment. The compounds described herein may be co-administered with one or more additional antiviral compounds, either as separate formulations, or as a combined formulation.

The antiviral compounds described herein may also be effectively administered with a traditional vaccine. Such vaccines may be prepared from live, attenuated, or killed virus as appropriate as well as subunit or recombinant vaccines.

During any of the processes for preparation of the antiviral compounds described herein, it may be necessary and/or desirable to protect sensitive or reactive groups on any of the molecules concerned. This may be achieved by means of conventional protecting groups, such as those described in Protective Groups in Organic Chemistry, ed. J. F. W. McOmie, Plenum Press, 1973; and 1, W. Greene & P. G. M. Wuts, Protective Groups in Organic Synthesis, John Wiley & Sons, 1999. The protecting groups may be removed at a convenient subsequent stage using methods known from the art.

The following examples illustrate suitable methods of synthesis of representative compounds described herein. However, the methods of synthesis are intended to illustrate and not to limit the invention to those exemplified below. The starting materials for preparing the antiviral compounds described herein are either commercially available or can be conveniently prepared according to one of the examples set forth below or otherwise using known chemistry procedures.

Example 1

General Synthetic Procedure

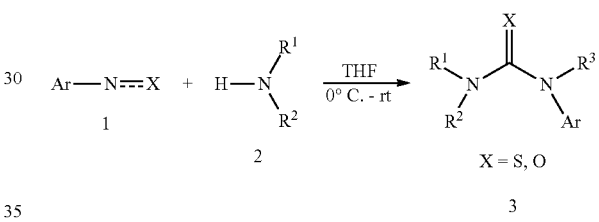

Compound 1 (phenyl isothiocyanate or phenyl isocyanate, 11.8 mMol) is dissolved in THF (20 mL) with ice-water codling under $N_2$. To the solution is added compound 2 (11.8 mMol) in THF (5 mL) drop by drop over 30 minutes. White solid precipitates in 5 minutes. The ice-water bath is removed and the suspension is further stirred at room temperature for 1 hr and then left standing in refrigerator for 3 hrs. Filtration of the mixture gives a white solid 3. The mother liquid is concentrated to 10 mL and then is left standing at rt overnight. Filtration gives a white crystalline solid (3). The combined solid is dried and weighted.

Example 2

Preparation of 4-Methyl-piperazine-1-carbothioic acid (3,4-dichlorophenyl)-amide

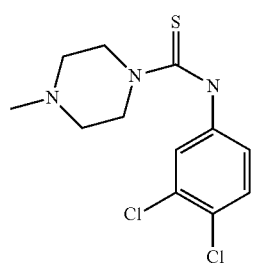 [SMILES: CN1CCN(C(=S)Nc2ccc(Cl)c(Cl)c2)CC1]

The compound is prepared according to the General Synthetic Procedure in Example 1 in 74%. $^1$H NMR in DMSO-$d_6$: δ 9.45 (s, 1H), 7.62 (d, 1H) 7.53 (d, 1H), 7.32 (dd, 1H), 3.88 (t, 4H), 2.37 (t, 4H), 2.21 (s, 3H).

Example 3

Inhibition of Arenaviral Replication

The ability of the compounds of described herein to inhibit Arenavirus was established by the following experimental procedure:

(a) Preparation of Virus Stock:

Virus stocks of arenavirus were prepared in Vero cells infected at low multiplicity (0.01 plaque forming units (PFU/cell) and harvested when cytopathic effects were complete. The samples were frozen and thawed and then sonicated to release cell-associated virus. The cell debris was removed by low-speed centrifugation, and the resulting virus suspension was stored in 1 mL aliquots at −80° C. The PFU/mL of the virus suspension was quantified by standard plaque assay on Vero cells.

(b) Arena CPE: Assay:

To determine the amount of arenavirus stock required to produce complete CPE in 7 days, Vero cell monolayers were seeded on to 96-well plates and infected with 2-fold serial dilutions of the arenavirus stock. At 7 days post-infection, the cultures were fixed with 5% glutaraldehyde and stained with 0.1% crystal violet. Virus-induced CPE was quantified spectrophotometrically at $OD_{570}$. From this analysis, a 1:1000 dilution of Tacaribe virus (TRVL 11573) stock was chosen for use in the HTS assay.

The results of these experiments indicated that the 96-well assay format was robust and reproducible. The S/N ratio (ratio of signal of cell control wells (signal) to virus control wells (noise)) was 9.2±1.8. The well-to-well and assay-to-assay variability was less than 20%. Based on this analysis, the 1:1000 dilution of Tacaribe virus was chosen for use in the assay.

(c) Compound Testing:

Representative compounds described herein were tested in the Tacaribe (TRVL 11573) virus CPE assay. Compounds were dissolved in DMSO and diluted in medium such that the final concentration in each well was 5 μM compound and 0.5% DMSO. The compounds are added robotically to the culture medium. Following compound addition, the cultures were infected with Tacaribe virus. After 7 days, plates were processed and CPE quantified as described.

Representative compounds described herein inhibited Tacaribe (TRVL 11573) virus-induced CPE by greater than 50% at the test concentration (5 μM). Selected compounds were further evaluated for potency ($EC_{50}$) in the CPE assay and cytotoxicity ($CC_{50}$) in an MITT assay. The MIT assay measures mitochondrial dehydrogenase activity in dividing cells. This method detects the in situ reduction of (3-(4,5-dimethylthiazol-2-yl)-5-(3-carboxymethoxyphenyl)-2-(4-sulfophenyl-)-2H-1-tetrazolium) using an electron coupling reagent (phenazine methosulfate) to produce an insoluble formazan. The absorbance of the formazan at 490 nm can be measured directly from 96-well assay plates following solubilization of the formazan in 50% ethanol. The quantity of formazan product is directly proportional to the number of living cells in culture.

The inhibitory concentration 50% ($EC_{50}$) values were determined from a plot of the compound inhibitory activity following the Tacaribe (TRVL 11573) CPE assay across eight compound concentrations (50, 16, 5, 1.6, 0.5, 0.16, 0.05 and 0.016 μM). All determinations were performed in duplicate. $EC_{50}$ values were calculated by comparing compound-treated and compound-untreated cells using a computer program. The EC value of the representative compound (the compound in Example 2) in the CPE assay is 140 nM. This antiviral is active at non-toxic concentrations.

Spectrum and Specificity of Activity of Compounds

Several additional CPE inhibition assays, similar to above, are utilized to identify a spectrum of activity of compounds of the compounds described herein within the arena genus. The $EC_{50}$ was calculated as the compound concentration required to reduce virus plaque numbers by 50%. Under BSL 4 conditions at USAMRIID the plaque reduction assays (with Lassa, Machupo, Guanarito, and Junin viruses) were performed as follows: 200 PFU of each virus was used to infect Vero cells. After virus adsorption, cell monolayers were rinsed and overlaid with complete medium containing 1% agarose and either lacking test compound or with different concentrations ranging from 15 μM to 0.05 μM. After 5 days incubation at 37° C., the monolayers were stained with neutral red and the numbers of plaques were counted.

The specificity of representative compounds for arena virus inhibition is reflected in the fact that they do not inhibit the replication of unrelated viruses, including Pichinde virus, Rift Valley fever virus (strain MP12), respiratory syncytial virus and cytomegalovirus.

Example 4

Approximately 400,000 compounds from an established compound library were tested in this assay. Assay plates were set up as follows. For the HTS CPE assay, Vero cells were plated at 80% confluency on 96-well plates. Test compounds (80 per plate) from the library were added to wells at a final concentration of 5 μM. Tacaribe virus was then added at a virus dilution that would result in 90% CPE after 7 days (pre-determined as a 1000-fold dilution of the virus stock; multiplicity of infection [MOI] approximately 0.001). Plates were incubated at 37° C. and 5% $CO_2$ for 7 days, then fixed with 5% glutaraldehyde and stained with 0.1% crystal violet. The extent of virus CPE was quantified spectrometrically at $OD_{570}$ using an Envision Microplate Reader. The inhibitory activity of each compound was calculated by subtracting from the $OD_{570}$ of test compound well from the average $OD_{570}$ of virus-infected cell wells, then dividing by the average $OD_{570}$ of mock-infected cell wells. The result represents the percent protection against Tacaribe virus CPE activity conferred by each compound. "Hits" in this assay were defined as compound that inhibited virus-induced CPE by greater than 50% at the test concentration (5 μM). Of the approximately 400,000 compounds screened in the Tacaribe virus HTS campaign, 2,347 hits were identified (0.58% hit rate).

Quality hits are defined as inhibitor compounds (hits) that exhibit acceptable chemical structures, antiviral potency and selectivity, and spectrum of antiviral activity. Specifically, compounds identified as hits in HTS assays (described above) were evaluated against four criteria: i) chemical tractability, ii) inhibitory potency, iii) inhibitory selectivity and, iv) antiviral specificity. Based on the HTS parameters, all hits have $EC_{50}$ values <5 μM. The chemical structures of compounds that met this initial criterion were visually examined for chemical tractability. A chemically tractable compound is defined as an entity that is synthetically accessible using reasonable chemical methodology, and which possesses chemically stable functionalities and (potential) drug-like qualities. Hits that passed this medicinal chemistry filter were evaluated for their inhibitory potency. $EC_{50}$ values were determined from a plot of the compound inhibitory activity, typically across eight compound concentrations (50, 16, 5, 1.6, 0.5, 0.16, 0.05 and 0.016 μM). To assess whether the hit is a selective inhibitor, the effect on cellular functions was determined using a standard cell proliferation assay. A 50% cytotoxicity concentration ($CC_{50}$) was determined using a tetrazolium-based colorimetric method, which measures the in situ reduction of 3-(4,5-dimethylthiazol-2-yl)-2,5-diphenyl tetrazolium bromide (MTT) to insoluble blue formazan crystals by mitochondrial enzymes in metabolically active cells. Solubilized crystals were quantified spectrometrically. Using the $EC_{50}$ and $CC_{50}$ values, a Selective Index (SI) was calculated ($SI=CC_{50}/EC_{50}$). Hits with Si values of at least 10 were considered further. The specificity of the antiviral activity exhibited by hit compounds was determined by testing the compounds against a number of related and unrelated viruses. Compounds are tested against a variety of unrelated DNA (HSV, CNN, vaccinia virus) and RNA (RSV, rotavirus, Rift Valley fever, Ebola virus, Ebola GP-pseudotype, Lassa GP-pseudotype, HIV env-pseudotype) viruses. Compounds described herein are selective against the selected original target virus and inactive against unrelated viruses.

| Compound number | $EC_{50}/CC_{50}$ μM Tacaribe | $EC_{50}/CC_{50}$ μM Candid 1 | $EC_{50}$ (μM) Category A NWA | Structure |
|---|---|---|---|---|
| 313761 | 0.14/50 | 0.26/50 | Machupo: 0.3 Guanarito: 0.15 | 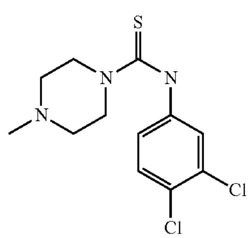 [SMILES: CN1CCN(C(=S)Nc2ccc(Cl)c(Cl)c2)CC1] |
| 280611 | 0.06/25 | 0.05/25 | Not tested | 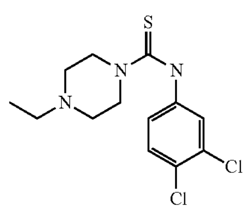 [SMILES: CCN1CCN(C(=S)Nc2ccc(Cl)c(Cl)c2)CC1] |
| 20013 | >50/>50 | >50/>50 | Not tested | 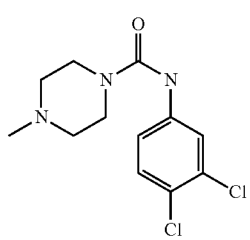 [SMILES: CN1CCN(C(=O)Nc2ccc(Cl)c(Cl)c2)CC1] |

Although the present invention has been described and exemplified in terms of certain preferred embodiments, other embodiments will be apparent to those skilled in the art. The invention is, therefore, not limited to the particular embodiments described and exemplified, but is capable of modification or variation without departing from the spirit of the invention, the full scope of which is delineated by the appended claims.

What we claim is:

1. A pharmaceutical composition comprising a pharmaceutically acceptable carrier and a pharmaceutically effective amount of a compound selected from the group consisting of 4-methyl-piperazine-1-carbothioic acid (3,4-dichloro-phenyl)-amide and 4-ethyl-piperazine-1-carbothioic acid (3,4-dichloro-phenyl)-amide, wherein said pharmaceutical composition is suitable for administration in a human or animal, wherein said administration is selected from the group consisting of: oral administration, rectal administration, parenteral administration, intravaginal administration, intraperitoneal administration and administration by inhalation.

2. A pharmaceutical composition comprising a pharmaceutically acceptable carrier and a pharmaceutically effective amount of a compound selected from the group consisting of 4-methyl-piperazine-1-carbothioic acid (3,4-dichloro-phenyl)-amide and 4-ethyl-piperazine-1-carbothioic acid (3,4-dichloro-phenyl)-amide and an additional antiviral agent selected from the group consisting of zidovudine, acyclovir, ganciclovir, vidarabidine, idoxuridine, trifluridine, foscarnet, interferon, amantadine, rimantadine, and ribavirin, wherein said pharmaceutical composition is suitable for administration in a human or animal, wherein said administration is selected from the group consisting of: oral administration, rectal administration, parenteral administration, intravaginal administration, intraperitoneal administration and administration by inhalation.

3. A pharmaceutical composition comprising a pharmaceutically acceptable carrier and a pharmaceutically effective amount of 4-methyl-piperazine-1-carbothioic acid (3,4-dichloro-phenyl)-amide, wherein said pharmaceutical composition is suitable for administration in a human or animal, wherein said administration is selected from the group consisting of: oral administration, rectal administration, parenteral administration, intravaginal administration, intraperitoneal administration and administration by inhalation.

4. A pharmaceutical composition comprising a pharmaceutically acceptable carrier and a pharmaceutically effective amount of 4-ethyl-piperazine-1-carbothioic acid (3,4-dichloro-phenyl)-amide, wherein said pharmaceutical composition is suitable for administration in a human or animal, wherein said administration is selected from the group consisting of: oral administration, rectal administration, parenteral administration, intravaginal administration, intraperitoneal administration and administration by inhalation.

5. The pharmaceutical composition of claim 1, wherein said pharmaceutically acceptable carrier is selected form the group consisting of solvents, diluents, dispersion aids, suspension aids, surface active agents, isotonic agents, thickening agents, emulsifying agents, preservatives, solid binders and lubricants.

6. The pharmaceutical composition of 1, wherein said pharmaceutically acceptable carrier is solid.

7. The pharmaceutical composition of 1, wherein said pharmaceutically acceptable carrier is liquid.

8. The pharmaceutical composition of claim 1, wherein said parenteral administration is selected from the group consisting of: intramuscular injection, subcutaneous injection and intravenous infusion.

* * * * *